United States Patent
Gao et al.

(10) Patent No.: US 7,794,996 B2
(45) Date of Patent: Sep. 14, 2010

(54) RECOMBINANT MURINE LEUKEMIA VIRUS REVERSE TRANSCRIPTASES, THE GENES ENCODING AND THE METHOD FOR EXPRESSING IT

(75) Inventors: Guangxia Gao, Beijing (CN); Shufeng Liu, Beijing (CN)

(73) Assignee: The Institute of Biophysics, Chinese Academy of Sciences, Beijing (CN)

( * ) Notice: Subject to any disclaimer, the term of this patent is extended or adjusted under 35 U.S.C. 154(b) by 788 days.

(21) Appl. No.: 10/585,863

(22) PCT Filed: Jan. 13, 2004

(86) PCT No.: PCT/CN2004/000039

§ 371 (c)(1),
(2), (4) Date: Feb. 7, 2007

(87) PCT Pub. No.: WO2005/071072

PCT Pub. Date: Aug. 4, 2005

(65) Prior Publication Data

US 2008/0131950 A1    Jun. 5, 2008

(51) Int. Cl.
| | |
|---|---|
| C12N 9/12 | (2006.01) |
| C12N 1/20 | (2006.01) |
| C12N 15/00 | (2006.01) |
| C12P 21/04 | (2006.01) |
| C12Q 1/68 | (2006.01) |
| C12Q 1/00 | (2006.01) |
| C07H 21/04 | (2006.01) |

(52) U.S. Cl. ............... 435/194; 435/4; 435/6; 435/69.1; 435/71.1; 435/252.3; 435/320.1; 435/440; 536/23.2

(58) Field of Classification Search ............ None
See application file for complete search history.

(56) References Cited

U.S. PATENT DOCUMENTS

| | | |
|---|---|---|
| 6,136,582 A | 10/2000 | Gao et al. |
| 2003/0021799 A1 | 1/2003 | Wilkinson et al. |

OTHER PUBLICATIONS

Jin et al. Analysis of the role of glutamine 190 in the catalytic mechanism of murine leukemia virus reverse transcriptase. J Biol Chem. Jul. 23, 1999;274(30):20861-8.*

Branden et al. Introduction to Protein Structure, Garland Publishing Inc., New York, p. 247, 1991.*

Kato et al. The entire nucleotide sequence of baboon endogenous virus DNA: a chimeric genome structure of murine type C and simian type D retroviruses. Jpn. J. Genet. 62, 127-137, 1987.*

* cited by examiner

*Primary Examiner*—Yong D Pak
(74) *Attorney, Agent, or Firm*—Sughrue Mion, PLLC (57) ABSTRACT

This invention provides recombinant murine leukemia virus reverse transcriptases, genes encoding these proteins and expression methods. The said murine leukemia virus reverse transcriptases are a series of MLV-RT proteins wherein the 84th amino acid residue (Q84) from the N-terminus is replaced with amino acid X, which is an amino acid with a side chain shorter than glutamine. The said murine leukemia virus reverse transcriptases have higher enzyme activity and processivity than the wild type enzyme, and are expected to be widely used in the field of biotechnology for cDNA synthesis.

7 Claims, 2 Drawing Sheets

MLV-RT-Q84N-D524N

SEQUENCE LISTING

```
<160> NUMBER OF SEQ ID NOS: 9

<210> SEQ ID NO 1
<211> LENGTH: 7488
<212> TYPE: DNA
<213> ORGANISM: artificial sequence
<220> FEATURE:
<223> OTHER INFORMATION: plasmid DNA

<400> SEQUENCE: 1
ccgacaccat cgaatggtgc aaaaccttttc gcggtatggc atgatagcgc ccggaagaga      60
gtcaattcag ggtggtgaat gtgaaaccag taacgttata cgatgtcgca gagtatgccg     120
```

-continued

| | |
|---|---|
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |
| ttgctgtgga agctgcctgc actaatgttc cggcgttatt tcttgatgtc tctgaccaga | 540 |
| cacccatcaa cagtattatt ttctcccatg aagacggtac gcgactgggc gtggagcatc | 600 |
| tggtcgcatt gggtcaccag caaatcgcgc tgttagcggg cccattaagt tctgtctcgg | 660 |
| cgcgtctgcg tctggctggc tggcataaat atctcactcg caatcaaatt cagccgatag | 720 |
| cggaacggga aggcgactgg agtgccatgt ccggttttca acaaaccatg caaatgctga | 780 |
| atgagggcat cgttcccact gcgatgctgg ttgccaacga tcagatggcg ctgggcgcaa | 840 |
| tgcgcgccat taccgagtcc gggctgcgcg ttggtgcgga tatctcggta gtgggatacg | 900 |
| acgataccga agacagctca tgttatatcc cgccgttaac caccatcaaa caggattttc | 960 |
| gcctgctggg gcaaaccagc gtggaccgct tgctgcaact ctctcagggc caggcggtga | 1020 |
| agggcaatca gctgttgccc gtctcactgg tgaaaagaaa aaccaccctg cgcccaata | 1080 |
| cgcaaaccgc ctctccccgc gcgttggccg attcattaat gcagctggca cgacaggttt | 1140 |
| cccgactgga aagcgggcag tgagcgcaac gcaattaatg tgagttagct cactcattag | 1200 |
| gcacaattct catgtttgac agcttatcat cgactgcacg gtgcaccaat gcttctggcg | 1260 |
| tcaggcagcc atcggaagct gtggtatggc tgtgcaggtc gtaaatcact gcataattcg | 1320 |
| tgtcgctcaa ggcgcactcc cgttctggat aatgtttttt gcgccgacat cataacggtt | 1380 |
| ctggcaaata ttctgaaatg agctgttgac aattaatcat cggctcgtat aatgtgtgga | 1440 |
| attgtgagcg gataacaatt tgaattctta agatttgtga ggggataaca atttcacaca | 1500 |
| ggaaacagaa tatgacccta aatatagaag atgagcatcg gctacatgag acctcaaaag | 1560 |
| agccagatgt ttctctaggg tccacatggc tgtctgattt tcctcaggcc tgggcggaaa | 1620 |
| ccggggggcat gggactggca gttcgccaag ctcctctgat catacctctg aaagcaacct | 1680 |
| ctaccccgt gtccataaaa caatacccca tgtcacaaga agccagactg gggatcaagc | 1740 |
| cccacataca gagactgttg gacgcgggaa ttctggtacc ctgccagtcc ccctggaaca | 1800 |
| cgccctgct acccgttaag aaaccaggga ctaatgatta taggcctgtc caggatctga | 1860 |
| gagaagtcaa caagcgggtg gaagacatcc accccaccgt gcccaaccct tacaacctct | 1920 |
| tgagcgggct cccaccgtcc caccagtggt acactgtgct tgatttaaag gatgccttt | 1980 |
| tctgcctgag actccacccc accagtcagc ctctcttcgc ctttgagtgg agagatccag | 2040 |
| agatgggaat ctcaggacaa ttgacctgga ccagactccc acagggtttc aaaaacagtc | 2100 |
| ccaccctgtt tgatgaggca ctgcacagag acctagcaga cttccggatc cagcacccag | 2160 |
| acttgatcct gctacagtac gtggatgact tactgctggc cgccacttct gagctagact | 2220 |
| gccaacaagg tactcgggcc ctgttacaaa ccctagggaa cctcgggtat cgggcctcgg | 2280 |
| ccaagaaagc ccaaatttgc cagaaacagg tcaagtatct ggggtatctt ctaaaagagg | 2340 |
| gtcagagatg gctgactgag gccagaaaag agactgtgat ggggcagcct actccgaaga | 2400 |
| cccctcgaca actaagggag ttcctaggga cggcaggctt ctgtcgcctc tggatccctg | 2460 |
| ggtttgcaga aatggcagcc cccttgtacc ctctcaccaa aacgggaact ctgttaatt | 2520 |

```
ggggcccaga ccaacaaaag gcctatcaag aaatcaagca agctcttcta actgcccag    2580 ccctggggtt gccagatttg actaagccct ttgaactctt tgtcgacgag aagcagggct    2640
acgccaaagg tgtcctaacg caaaaactgg gaccttggcg tcggccgtg gcctacctgt    2700 ccaaaaagct agacccagta gcagctgggt ggccccttg cctacggatg gtagcagcca    2760
ttgccgtact gacaaaggat gcaggcaagc taaccatggg acagccacta gtcattctgg    2820 cccccatgc agtagaggca ctagtcaaac aaccccccga ccgctggctt ccaacgccc    2880 ggatgactca ctatcaggcc ttgcttttgg acacggaccg gtccagttc ggaccggtgg    2940 tagccctgaa cccggctacg ctgctcccac tgcctgagga agggctgcaa cacaactgcc    3000
ttgatatcct ggccgaagcc cacggaaccc gacccgacct aacggaccag ccgctcccag    3060
acgccgacca cacctggtac acgaatggaa gcagtctctt acaagaggga cagcgtaagg    3120
cgggagctgc ggtgaccacc gagaccgagg taatctgggc taaagccctg ccagccggga    3180
catccgctca gcgggctgaa ctgatagcac tcacccaggc cctaaagatg gcagaaggta    3240
agaagctaaa tgtttatact gatagccgtt atgcttttgc tactgcccat atccatggag    3300
aaatatacag aaggcgtggg ttgctcacat cagaaggcaa agagatcaaa aataaagacg    3360
agatcttggc cctactaaaa gccctctttc tgcccaaaag acttagcata atccattgtc    3420
caggacatca aaagggacac agccgcgagg ctagaggcaa ccggatggct gaccaagcgg    3480
cccgaaaggc agccatcaca gagactccag acacctctac cctcctccat caccatcacc    3540
atcactagtc tagagtcgac ctgcaggcaa gcttggcact ggccgtcgtt ttacaacgtc    3600
gtgactggga aaaccctggc gttacccaac ttaatcgcct tgcagcacat ccccctttcg    3660
ccagctggcg taatagcgaa gaggcccgca ccgatcgccc ttcccaacag ttgcgcagcc    3720
tgaatggcga atggcagctt ggctgttttg gcggatgaga taagattttc agcctgatac    3780
agattaaatc agaacgcaga gcggtctga taaaacagaa tttgcctggc ggcagtagcg    3840
cggtggtccc acctgacccc atgccgaact cagaagtgaa acgccgtagc gccgatggta    3900
gtgtggggtc tccccatgcg agagtaggga actgccaggc atcaaataaa acgaaaggct    3960
cagtcgaaag actgggcctt tcgttttatc tgttgtttgt cggtgaacgc tctcctgagt    4020
aggacaaatc cgccgggagc ggatttgaac gttgcgaagc aacggcccgg agggtggcgg    4080
gcaggacgcc cgccataaac tgccaggcat caaattaagc agaaggccat cctgacggat    4140
ggcctttttg cgtttctaca aactctttt gtttattttt ctaaatacat tcaaatatgt    4200
atccgctcat gagacaataa ccctgataaa tgcttcaata atattgaaaa aggaagagta    4260
tgagtattca acatttccgt gtcgccctta ttccctttt tgcggcattt tgccttcctg    4320
tttttgctca cccagaaacg ctggtgaaag taaaagatgc tgaagatcag ttgggtgcac    4380
gagtgggtta catcgaactg gatctcaaca gcggtaagat ccttgagagt tttcgccccg    4440
aagaacgttc tccaatgatg agcactttta aagttctgct atgtggcgcg gtattatccc    4500
gtgttgacgc cgggcaagag caactcggtc gccgcataca ctattctcag aatgacttgg    4560
ttgagtactc accagtcaca gaaaagcatc ttacggatgg catgacagta agagaattat    4620
gcagtgctgc cataaccatg agtgataaca ctgcggccaa cttacttctg acaacgatcg    4680
gaggaccgaa ggagctaacc gcttttttgc acaacatggg ggatcatgta actcgccttg    4740
atcgttggga accggagctg aatgaagcca taccaaacga cgagcgtgac accacgatgc    4800
ctgtagcaat ggcaacaacg ttgcgcaaac tattaactgg cgaactactt actctagctt    4860
```

-continued

```
cccggcaaca attaatagac tggatggagg cggataaagt tgcaggacca cttctgcgct    4920
cggcccttcc ggctggctgg tttattgctg ataaatctgg agccggtgag cgtgggtctc    4980
gcggtatcat tgcagcactg gggccagatg gtaagccctc ccgtatcgta gttatctaca    5040
cgacggggag tcaggcaact atggatgaac gaaatagaca gatcgctgag ataggtgcct    5100
cactgattaa gcattggtaa ctgtcagacc aagtttactc atatatactt tagattgatt    5160
taccccggtt gataatcaga aaagccccaa aaacaggaag attgtataag caaatattta    5220
aattgtaaac gttaatattt tgttaaaatt cgcgttaaat ttttgttaaa tcagctcatt    5280
ttttaaccaa taggccgaaa tcggcaaaat cccttataaa tcaaaagaat agcccgagat    5340
agggttgagt gttgttccag tttggaacaa gagtccacta ttaaagaacg tggactccaa    5400
cgtcaaaggg cgaaaaaccg tctatcaggg cgatggccca ctacgtgaac catcacccaa    5460
atcaagtttt tggggtcga ggtgccgtaa agcactaaat cggaaccct a aagggagccc    5520 ccgatttaga gcttgacggg gaaagccggc gaacgtggcg agaaaggaag gaagaaagc    5580 gaaaggagcg ggcgctaggg cgctggcaag tgtagcggtc acgctgcgcg taaccaccac    5640
acccgccgcg cttaatgcgc cgctacaggg cgcgtaaaag gatctaggtg aagatccttt    5700
ttgataatct catgaccaaa atcccttaac gtgagttttc gttccactga gcgtcagacc    5760
ccgtagaaaa gatcaaagga tcttcttgag atccttttt tctgcgcgta atctgctgct    5820
tgcaaacaaa aaaaccaccg ctaccagcgg tggtttgttt gccggatcaa gagctaccaa    5880 ctcttttcc gaaggtaact ggcttcagca gagcgcagat accaaatact gtccttctag    5940
tgtagccgta gttaggccac cacttcaaga actctgtagc accgcctaca tacctcgctc    6000
tgctaatcct gttaccagtg gctgctgcca gtggcgataa gtcgtgtctt accgggttgg    6060
actcaagacg atagttaccg gataaggcgc agcggtcggg ctgaacgggg ggttcgtgca    6120
cacagcccag cttggagcga acgacctaca ccgaactgag atacctacag cgtgagctat    6180
gagaaagcgc cacgcttccc gaagggagaa aggcggacag gtatccggta agcggcaggg    6240
tcggaacagg agagcgcacg agggagcttc caggggggaaa cgcctggtat ctttatagtc    6300
ctgtcgggtt tcgccacctc tgacttgagc gtcgattttt gtgatgctcg tcagggggggc    6360 ggagcctatg gaaaaacgcc agcaacgcgg cctttttacg gttcctggcc ttttgctggc    6420
cttttgctca catgttcttt cctgcgttat cccctgattc tgtggataac cgtattaccg    6480
cctttgagtg agctgatacc gctcgccgca gccgaacgac cgagcgcagc gagtcagtga    6540
gcgaggaagc ggaagagcgc ctgatgcggt attttctcct tacgcatctg tgcggtattt    6600
cacaccgcat atggtgcact ctcagtacaa tctgctctga tgccgcatag ttaagccagt    6660
atacactccg ctatcgctac gtgactgggt catggctgcg ccccgacacc cgccaacacc    6720
cgctgacgcg ccctgacggg cttgtctgct cccggcatcc gcttacagac aagctgtgac    6780
cgtctccggg agctgcatgt gtcagaggtt ttcaccgtca tcaccgaaac gcgcgaggca    6840
gctgcggtaa agctcatcag cgtggtcgtg cagcgattca cagatgtctg cctgttcatc    6900
cgcgtccagc tcgttgagtt tctccagaag cgttaatgtc tggcttctga taaagcgggc    6960
catgttaagg gcggtttttt cctgtttggt cacttgatgc ctccgtgtaa ggggggaattt    7020 ctgttcatgg gggtaatgat accgatgaaa cgagagagga tgctcacgat acggttact    7080 gatgatgaac atgcccggtt actggaacgt tgtgagggta aacaactggc ggtatggatg    7140
cggcgggacc agagaaaaat cactcagggt caatgccagc gcttcgttaa tacagatgta    7200
ggtgttccac agggtagcca gcagcatcct gcgatgcaga tccggaacat aatggtgcag    7260
```

-continued

```
ggcgctgact tccgcgtttc cagactttac gaaacacgga aaccgaagac cattcatgtt    7320
gttgctcagg tcgcagacgt tttgcagcag cagtcgcttc acgttcgctc gcgtatcggt    7380
gattcattct gctaaccagt aaggcaaccc cgccagccta gccgggtcct caacgacagg    7440
agcacgatca tgcgcacccg tggccaggac ccaacgctgc ccgaaatt                 7488
```

<210> SEQ ID NO 2
<211> LENGTH: 671
<212> TYPE: PRT
<213> ORGANISM: artificial sequence
<220> FEATURE:
<223> OTHER INFORMATION: reverse transcriptase

<400> SEQUENCE: 2

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Ala Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320
```

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
                370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
                435                 440                 445

Asp Arg Trp Leu Ser Asn Ala Arg Met Thr His Tyr Gln Ala Leu Leu
                450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asn Gly Ser Ser Leu
                515                 520                 525

Leu Gln Glu Gly Gln Arg Lys Ala Gly Ala Ala Val Thr Thr Glu Thr
                530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Arg Gly Leu Leu Thr Ser Glu Gly
                595                 600                 605

Lys Glu Ile Lys Asn Lys Asp Glu Ile Leu Ala Leu Leu Lys Ala Leu
                610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
                660                 665                 670

<210> SEQ ID NO 3
<211> LENGTH: 7488
<212> TYPE: DNA
<213> ORGANISM: artificial sequence
<220> FEATURE:
<223> OTHER INFORMATION: plasmid DNA

<400> SEQUENCE: 3
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120

-continued

```
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga    1020
agggcaatca gctgttgccc gtctcactgg tgaaaagaaa accaccctg cgcccaata     1080
cgcaaaccgc ctctccccgc gcgttggccg attcattaat gcagctggca cgacaggttt    1140
cccgactgga aagcgggcag tgagcgcaac gcaattaatg tgagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga    1440
attgtgagcg gataacaatt tgaattctta agatttgtga ggggataaca atttcacaca    1500
ggaaacagaa tatgacccta aatatagaag atgagcatcg gctacatgag acctcaaaag    1560
agccagatgt ttctctaggg tccacatggc tgtctgattt tcctcaggcc tgggcggaaa    1620
ccggggggcat gggactggca gttcgccaag ctcctctgat catacctctg aaagcaacct    1680
ctaccccccgt gtccataaaa caataccccca tgtcacaaga agccagactg gggatcaagc    1740
cccacataca gagactgttg gacaacggga tcctggtacc ctgccagtcc ccctggaaca    1800
cgccctgct acccgttaag aaaccaggga ctaatgatta taggcctgtc caggatctga    1860
gagaagtcaa caagcgggtg gaagacatcc accccaccgt gcccaaccct tacaacctct    1920
tgagcgggct cccaccgtcc caccagtggt acactgtgct tgatttaaag gatgccttt     1980
tctgcctgag actccaccccc accagtcagc ctctcttcgc ctttgagtgg agagatccag    2040
agatgggaat ctcaggacaa ttgacctgga ccagactccc acagggtttc aaaaacagtc    2100
ccaccctgtt tgatgaggca ctgcacagag acctagcaga cttccggatc cagcacccag    2160
acttgatcct gctacagtac gtggatgact tactgctggc cgccacttct gagctagact    2220
gccaacaagg tactcgggcc ctgttacaaa ccctagggaa cctcgggtat cgggcctcgg    2280
ccaagaaagc ccaaatttgc cagaaacagg tcaagtatct ggggtatctt ctaaaagagg    2340
gtcagagatg gctgactgag gccagaaaag agactgtgat ggggcagcct actccgaaga    2400
cccctcgaca actaagggag ttcctaggga cggcaggctt ctgtcgcctc tggatccctg    2460
```

```
ggtttgcaga aatggcagcc cccttgtacc ctctcaccaa aacgggggact ctgtttaatt      2520
ggggcccaga ccaacaaaag gcctatcaag aaatcaagca agctcttcta actgcccccag     2580
ccctgggggtt gccagatttg actaagcccct ttgaactctt tgtcgacgag aagcagggct    2640
acgccaaagg tgtcctaacg caaaaactgg gaccttggcg tcggccggtg gcctacctgt     2700
ccaaaaagct agacccagta gcagctgggt ggcccccttg cctacggatg gtagcagcca     2760
ttgccgtact gacaaaggat gcaggcaagc taaccatggg acagccacta gtcattctgg     2820
ccccccatgc agtagaggca ctagtcaaac aaccccccga ccgctggctt ccaacgccc      2880
ggatgactca ctatcaggcc ttgcttttgg acacggaccg ggtccagttc ggaccggtgg     2940
tagccctgaa cccggctacg ctgctcccac tgcctgagga agggctgcaa cacaactgcc    3000
ttgatatcct ggccgaagcc cacgaaccc gacccgacct aacggaccag ccgctcccag     3060
acgccgacca cacctggtac acgaatggaa gcagtctctt acaagaggga cagcgtaagg   3120
cgggagctgc ggtgaccacc gagaccgagg taatctgggc taaagccctg ccagccggga    3180
catccgctca gcgggctgaa ctgatagcac tcacccaggc cctaaagatg gcagaaggta    3240
agaagctaaa tgtttatact gatagccgtt atgcttttgc tactgcccat atccatggag     3300
aaatatacag aaggcgtggg ttgctcacat cagaaggcaa agagatcaaa aataaagacg    3360
agatcttggc cctactaaaa gccctctttc tgcccaaaag acttagcata tccattgtc    3420
caggacatca aagggacac agcgccgagg ctagaggcaa ccggatggct gaccaagcgg     3480
cccgaaaggc agccatcaca gagactccag acacctctac cctcctccat caccatcacc   3540
atcactagtc tagagtcgac ctgcaggcaa gcttggcact ggccgtcgtt ttacaacgtc    3600
gtgactggga aaaccctggc gttacccaac ttaatcgcct tgcagcacat cccccttttcg   3660
ccagctggcg taatagcgaa gaggcccgca ccgatcgccc ttcccaacag ttgcgcagcc    3720
tgaatggcga atggcagctt ggctgttttg gcggatgaga taagattttc agcctgatac    3780
agattaaatc agaacgcaga agcggtctga taaaacagaa tttgcctggc ggcagtagcg    3840
cggtggtccc cctgaccccc atgccgaact cagaagtgaa acgccgtagc gccgatggta    3900
gtgtggggtc tccccatgcg agagtaggga actgccaggc atcaaataaa acgaaaggct    3960
cagtcgaaag actgggcctt tcgttttatc tgttgtttgt cggtgaacgc tctcctgagt    4020
aggacaaatc cgccgggagc ggatttgaac gttgcgaagc aacggcccgg agggtggcgg    4080
gcaggacgcc cgccataaac tgccaggcat caaattaagc agaaggccat cctgacggat    4140
ggcctttttg cgtttctaca aactctttt gtttattttt ctaaatacat tcaaatatgt    4200
atccgctcat gagacaataa ccctgataaa tgcttcaata atattgaaaa aggaagagta    4260
tgagtattca acatttccgt gtcgccctta ttcccttttt tgcggcattt tgccttcctg    4320
tttttgctca cccagaaacg ctggtgaaag taaaagatgc tgaagatcag ttgggtgcac   4380
gagtgggtta catcgaactg gatctcaaca gcggtaagat ccttgagagt tttcgccccg    4440
aagaacgttc tccaatgatg agcactttta aagttctgct atgtggcgcg gtattatccc    4500
gtgttgacgc cggggcaagag caactcggtc gccgcataca ctattctcag aatgacttgg   4560
ttgagtactc accagtcaca gaaaagcatc ttacggatgg catgacagta agagaattat    4620
gcagtgctgc cataaccatg agtgataaca ctgcggccaa cttacttctg acaacgatcg    4680
gaggaccgaa ggagctaacc gcttttttgc acaacatggg ggatcatgta actcgccttg    4740
atcgttggga accggagctg aatgaagcca taccaaacga cgagcgtgac accacgatgc    4800
ctgtagcaat ggcaacaacg ttgcgcaaac tattaactgg cgaactactt actctagctt   4860
```

-continued

```
cccggcaaca attaatagac tggatggagg cggataaagt tgcaggacca cttctgcgct    4920
cggcccttcc ggctggctgg tttattgctg ataaatctgg agccggtgag cgtgggtctc    4980
gcggtatcat tgcagcactg gggccagatg gtaagccctc ccgtatcgta gttatctaca    5040
cgacggggag tcaggcaact atggatgaac gaaatagaca gatcgctgag ataggtgcct    5100
cactgattaa gcattggtaa ctgtcagacc aagtttactc atatatactt tagattgatt    5160
taccccggtt gataatcaga aaagccccaa aaacaggaag attgtataag caaatattta    5220
aattgtaaac gttaatattt tgttaaaatt cgcgttaaat ttttgttaaa tcagctcatt    5280
ttttaaccaa taggccgaaa tcggcaaaat cccttataaa tcaaaagaat agcccgagat    5340
agggttgagt gttgttccag tttggaacaa gagtccacta ttaaagaacg tggactccaa    5400
cgtcaaaggg cgaaaaaccg tctatcaggg cgatggccca ctacgtgaac catcacccaa    5460
atcaagtttt tggggtcga ggtgccgtaa agcactaaat cggaacccta agggagcccc    5520
ccgatttaga gcttgacggg gaaagccggc gaacgtggcg agaaaggaag ggaagaaagc    5580
gaaaggagcg ggcgctaggg cgctggcaag tgtagcggtc acgctgcgcg taaccaccac    5640
acccgccgcg cttaatgcgc cgctacaggg cgcgtaaaag gatctaggtg aagatccttt    5700
ttgataatct catgaccaaa atcccttaac gtgagttttc gttccactga gcgtcagacc    5760
ccgtagaaaa gatcaaagga tcttcttgag atccttttt tctgcgcgta atctgctgct    5820
tgcaaacaaa aaaaccaccg ctaccagcgg tggtttgttt gccggatcaa gagctaccaa    5880
ctctttttcc gaaggtaact ggcttcagca gagcgcagat accaaatact gtccttctag    5940
tgtagccgta gttaggccac cacttcaaga actctgtagc accgcctaca tacctcgctc    6000
tgctaatcct gttaccagtg gctgctgcca gtggcgataa gtcgtgtctt accgggttgg    6060
actcaagacg atagttaccg gataaggcgc agcggtcggg ctgaacgggg ggttcgtgca    6120
cacagcccag cttggagcga acgacctaca ccgaactgag atacctacag cgtgagctat    6180
gagaaagcgc cacgcttccc gaagggagaa aggcggacag gtatccggta agcggcaggg    6240
tcggaacagg agagcgcacg agggagcttc caggggggaaa cgcctggtat ctttatagtc    6300
ctgtcgggtt tcgccacctc tgacttgagc gtcgattttt gtgatgctcg tcagggggc    6360 ggagcctatg gaaaaacgcc agcaacgcgg cctttttacg gttcctggcc ttttgctggc    6420
cttttgctca catgttcttt cctgcgttat cccctgattc tgtggataac cgtattaccg    6480
cctttgagtg agctgatacc gctcgccgca gccgaacgac cgagcgcagc gagtcagtga    6540
gcgaggaagc ggaagagcgc ctgatgcggt attttctcct tacgcatctg tgcggtattt    6600
cacaccgcat atggtgcact ctcagtacaa tctgctctga tgccgcatag ttaagccagt    6660
atacactccg ctatcgctac gtgactgggt catggctgcg ccccgacacc cgccaacacc    6720
cgctgacgcg ccctgacggg cttgtctgct cccggcatcc gcttacagac aagctgtgac    6780
cgtctccggg agctgcatgt gtcagaggtt ttcaccgtca tcaccgaaac gcgcgaggca    6840
gctgcggtaa agctcatcag cgtggtcgtg cagcgattca cagatgtctg cctgttcatc    6900
cgcgtccagc tcgttgagtt tctccagaag cgttaatgtc tggcttctga taaagcgggc    6960
catgttaagg gcggtttttt cctgtttggt cacttgatgc ctccgtgtaa ggggaattt    7020 ctgttcatgg gggtaatgat accgatgaaa cgagagagga tgctcacgat acgggttact    7080
gatgatgaac atgcccggtt actggaacgt tgtgagggta aacaactggc ggtatggatg    7140
cggcgggacc agagaaaaat cactcagggt caatgccagc gcttcgttaa tacagatgta    7200
```

-continued

```
ggtgttccac agggtagcca gcagcatcct gcgatgcaga tccggaacat aatggtgcag    7260
ggcgctgact tccgcgtttc cagactttac gaaacacgga aaccgaagac cattcatgtt    7320
gttgctcagg tcgcagacgt tttgcagcag cagtcgcttc acgttcgctc gcgtatcggt    7380
gattcattct gctaaccagt aaggcaaccc cgccagccta gccgggtcct caacgacagg    7440
agcacgatca tgcgcacccg tggccaggac ccaacgctgc ccgaaatt                 7488
```

<210> SEQ ID NO 4
<211> LENGTH: 671
<212> TYPE: PRT
<213> ORGANISM: artificial sequence
<220> FEATURE:
<223> OTHER INFORMATION: reverse transcriptase

<400> SEQUENCE: 4

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Asn Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320
```

```
Ala Ala Pro Leu Tyr Pro Leu Thr Lys Thr Gly Thr Leu Phe Asn Trp
            325                 330                 335

Gly Pro Asp Gln Gln Lys Ala Tyr Gln Glu Ile Lys Gln Ala Leu Leu
        340                 345                 350

Thr Ala Pro Ala Leu Gly Leu Pro Asp Leu Thr Lys Pro Phe Glu Leu
    355                 360                 365

Phe Val Asp Glu Lys Gln Gly Tyr Ala Lys Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
                435                 440                 445

Asp Arg Trp Leu Ser Asn Ala Arg Met Thr His Tyr Gln Ala Leu Leu
            450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asn Gly Ser Ser Leu
            515                 520                 525

Leu Gln Glu Gly Gln Arg Lys Ala Gly Ala Ala Val Thr Thr Glu Thr
            530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670

<210> SEQ ID NO 5
<211> LENGTH: 17
<212> TYPE: DNA
<213> ORGANISM: artificial sequence
<220> FEATURE:
<223> OTHER INFORMATION: primer

<400> SEQUENCE: 5
gtggaattgt gagccga                                                17
```

<210> SEQ ID NO 6
<211> LENGTH: 29
<212> TYPE: DNA
<213> ORGANISM: artificial sequence
<220> FEATURE:
<223> OTHER INFORMATION: primer

<400> SEQUENCE: 6
cggaattccc gcgtccaaca gtctctgta                                29

<210> SEQ ID NO 7
<211> LENGTH: 17
<212> TYPE: DNA
<213> ORGANISM: artificial sequence
<220> FEATURE:
<223> OTHER INFORMATION: primer

<400> SEQUENCE: 7
tgggagtctg gtccagg                                             17

<210> SEQ ID NO 8
<211> LENGTH: 24
<212> TYPE: DNA
<213> ORGANISM: artificial sequence
<220> FEATURE:
<223> OTHER INFORMATION: primer

<400> SEQUENCE: 8
cggaattctg gtaccctgcc agtc                                     24

<210> SEQ ID NO 9
<211> LENGTH: 671
<212> TYPE: PRT
<213> ORGANISM: artificial sequence
<220> FEATURE:
<223> OTHER INFORMATION: reverse transcriptase

<400> SEQUENCE: 9

```
Thr Leu Asn Ile Glu Asp Glu His Arg Leu His Glu Thr Ser Lys Glu
 1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175
```

-continued

```
Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
```

-continued

```
                 595                     600                     605
Lys Glu Ile Lys Asn Lys Asp Glu Ile Leu Ala Leu Leu Lys Ala Leu
        610                     615                     620

Phe Leu Pro Lys Arg Leu Ser Ile Ile His Cys Pro Gly His Gln Lys
625                     630                     635                     640

Gly His Ser Ala Glu Ala Arg Gly Asn Arg Met Ala Asp Gln Ala Ala
                645                     650                     655

Arg Lys Ala Ala Ile Thr Glu Thr Pro Asp Thr Ser Thr Leu Leu
                660                     665                     670
```

RECOMBINANT MURINE LEUKEMIA VIRUS REVERSE TRANSCRIPTASES, THE GENES ENCODING AND THE METHOD FOR EXPRESSING IT

TECHNOLOGY CATEGORY

This invention involves recombinant reverse transcriptases, their coding genes and expression methods in the field of biotechnology. This invention particularly involves recombinant murine leukemia virus reverse transcriptases, their coding genes and expression methods.

BACKGROUND OF THE INVENTION

Reverse transcriptase (RT) is a kind of DNA polymerase encoded by retroviruses, which can synthesize DNA using DNA or RNA as template. Reverse transcriptase, which can convert RNA into cDNA, is widely used in molecular biology, including constructing cDNA libraries and analyzing the amount of RNA in biological samples by RT-PCR. Nowadays the dominant RT in the market is murine leukemia virus reverse transcriptase (MLV-RT).

MLV-RT is composed of two functional domains, a DNA polymerase domain at the N-terminus and a ribonuclease (RNase) H domain at the C-terminus. These two domains can be expressed separately without affecting the function of each other. The first generation of recombinant MLV-RT used in cDNA synthesis contained only the DNA polymerase domain, with the RNase H domain deleted. Though the enzymatic activity is similar to that of full-length MLV-RT, its processivity is relatively poor, resulting in short cDNAs. It was found that although the RNase H domain does not affect the DNA polymerase activity of MLV-RT, it affects the enzyme's processivity. The reason is that the RNase H domain binds to the template/primer complex, and thereby increases the enzyme's affinity for the template/primer. When the $524^{th}$ Asp, a key residue in the RNase H active site, is replaced with Asn by site-directed mutagenesis, the resulting mutant enzyme, MLV-RT-D524N, does not demonstrate any RNase H activity, but retains the DNA polymerase activity and high affinity for the template/primer. This mutant enzyme, which is patented by Invitrogen under trade mark Superscript II, is currently widely used. However, this mutant enzyme is still not perfect; its processivity is still not ideal and the most common problem encountered is the formation of short, less than full-length products.

SUMMARY OF THE INVENTION

This invention provides murine leukemia virus reverse transcriptases, named MLV-RT-Q84X, wherein the 84th amino acid residue (Q84) from the N-terminus (i.e., Thr Leu Asn Ile Glu Asp Glu His Arg Leu His Glu Thr Ser Lys Glu Pro Asp Val Ser Leu Gly Ser Thr Trp Leu Ser Asp Phe Pro Gln Ala Trp Ala Glu Thr Gly Gly Met Gly Leu Ala Val Arg Gln Ala Pro Leu Ile Ile Pro Leu Lys Ala Thr Ser Thr Pro Val Ser Ile Lys Gln Tyr Pro Met Ser Gln Glu Ala Arg Leu Gly Ile Lys Pro His Ile Gln Arg Leu Leu Asp Gln Gly Ile Leu Val Pro Cys Gln Ser Pro Trp Asn Thr Pro Leu Leu Pro Val Lys Lys Pro Gly Thr Asn Asp Tyr Arg Pro Val Gln Asp Leu Arg Glu Val Asn Lys Arg Val Glu Asp Ile His Pro Thr Val Pro Asn Pro Tyr Asn Leu Leu Ser Gly Leu Pro Pro Ser His Gln Trp Tyr Thr Val Leu Asp Leu Lys Asp Ala Phe Phe Cys Leu Arg Leu His Pro Thr Ser Gln Pro Leu Phe Ala Phe Glu Trp Arg Asp Pro Glu Met Gly Ile Ser Gly Gln Leu Thr Trp Thr Arg Leu Pro Gln Gly Phe Lys Asn Ser Pro Thr Leu Phe Asp Glu Ala Leu His Arg Asp Leu Ala Asp Phe Arg Ile Gln His Pro Asp Leu Ile Leu Leu Gln Tyr Val Asp Asp Leu Leu Leu Ala Ala Thr Ser Glu Leu Asp Cys Gln Gln Gly Thr Arg Ala Leu Leu Gln Thr Leu Gly Asn Leu Gly Tyr Arg Ala Ser Ala Lys Lys Ala Gln Ile Cys Gln Lys Gln Val Lys Tyr Leu Gly Tyr Leu Leu Lys Glu Gly Gln Arg Trp Leu Thr Glu Ala Arg Lys Glu Thr Val Met Gly Gln Pro Thr Pro Lys Thr Pro Arg Gln Leu Arg Glu Phe Leu Gly Thr Ala Gly Phe Cys Arg Leu Trp Ile Pro Gly Phe Ala Glu Met Ala Ala Pro Leu Tyr Pro Leu Thr Lys Thr Gly Thr Leu Phe Asn Trp Gly Pro Asp Gln Gln Lys Ala Tyr Gln Glu Ile Lys Gln Ala Leu Leu Thr Ala Pro Ala Leu Gly Leu Pro Asp Leu Thr Lys Pro Phe Glu Leu Phe Val Asp Glu Lys Gln Gly Tyr Ala Lys Gly Val Leu Thr Gln Lys Leu Gly Pro Trp Arg Arg Pro Val Ala Tyr Leu Ser Lys Lys Leu Asp Pro Val Ala Ala Gly Trp Pro Pro Cys Leu Arg Met Val Ala Ala Ile Ala Val Leu Thr Lys Asp Ala Gly Lys Leu Thr Met Gly Gln Pro Leu Val Ile Leu Ala Pro His Ala Val Glu Ala Leu Val Lys Gln Pro Pro Asp Arg Trp Leu Ser Asn Ala Arg Met Thr His Tyr Gln Ala Leu Leu Leu Asp Thr Asp Arg Val Gln Phe Gly Pro Val Val Ala Leu Asn Pro Ala Thr Leu Leu Pro Leu Pro Glu Glu Gly Leu Gln His Asn Cys Leu Asp Ile Leu Ala Glu Ala His Gly Thr Arg Pro Asp Leu Thr Asp Gln Pro Leu Pro Asp Ala Asp His Thr Trp Tyr Thr Asp Gly Ser Ser Leu Leu Gln Glu Gly Gln Arg Lys Ala Gly Ala Ala Val Thr Thr Glu Thr Glu Val Ile Trp Ala Lys Ala Leu Pro Ala Gly Thr Ser Ala Gln Arg Ala Glu Leu Ile Ala Leu Thr Gln Ala Leu Lys Met Ala Glu Gly Lys Lys Leu Asn Val Tyr Thr Asp Ser Arg Tyr Ala Phe Ala Thr Ala His Ile His Gly Glu Ile Tyr Arg Arg Arg Gly Leu Leu Thr Ser Glu Gly Lys Glu Ile Lys Asn Lys Asp Glu Ile Leu Ala Leu Leu Lys Ala Leu Phe Leu Pro Lys Arg Leu Ser Ile Ile His Cys Pro Gly His Gln Lys Gly His Ser Ala Glu Ala Arg Gly Asn Arg Met Ala Asp Gln Ala Ala Arg Lys Ala Ala Ile Thr Glu Thr Pro Asp Thr Ser Thr Leu Leu, see SEQ ID NO:9), wild type, is replaced with X, which represents a residue with a side chain shorter than that of glutamine.

The invention further provides murine leukemia virus reverse transcriptases, named MLVRT-Q84X-D524N, wherein the $524^{th}$ aspartic acid residue from the N-terminus is replaced with asparagines (Asn), and the $84^{th}$ amino acid residue (Q84) from the N-terminus is replaced with X, which represents a residue with a side chain shorter than that of glutamine.

The invention further provides murine leukaemia virus reverse transcriptases, MLV-RT-Q84X and MLV-RT-Q84X-D524N, wherein X is preferably chosen from alanine (Ala), serine (Ser), asparagine (Asn), or aspartic acid (Asp). Alanine is especially favoured.

The invention further provides the coding sequences of the recombinant murine leukemia virus reverse transcriptases.

The invention further provides a method of expressing the recombinant murine leukemia virus reverse transcriptases comprising: a) transforming the murine leukaemia virus reverse transcriptases expressing plasmids into *Escherichia coli*; b) culturing the clones to express recombinant murine leukemia virus reverse transcriptases. These recombinant murine leukemia virus reverse transcriptases are a series of MLV-RT proteins wherein the $84^{th}$ amino acid residue (Q84) from N-terminus is replaced by a residue that has a side chain shorter than that of glutamine.

The invention also provides a method of expressing the recombinant murine leukemia virus reverse transcriptases comprising: a) transforming the murine leukaemia virus reverse transcriptases expressing plasmids into *Escherichia coli*; b) culturing the clones to express recombinant murine leukemia virus reverse transcriptases. These recombinant murine leukemia virus reverse transcriptases are a series of MLV-RT proteins wherein the $524^{th}$ aspartic acid residue from the N-terminus is replaced with asparagine, and the $84^{th}$ amino acid residue (Q84) from N-terminus is replaced by a residue that has a side chain shorter than that of glutamine. The 84$^{th}$ amino acid is preferably replaced by alalnine.

The invention further provides nucleotide sequences of plasmids pTacRT-Q84N-D524N and TacRT-Q84A-D524N as described in SEQ ID NO: 1 and SEQ ID NO: 3, respectively. pTacRT-Q84N-D524N and TacRT-Q84A-D524N express murine leukaemia virus reverse transcriptases with amino acid sequences described in SEQ ID NO: 2 and SEQ ID NO: 4, respectively. The host cell expressing these proteins is *Escherichia coli* BL21. Both SEQ ID NO: 1 and SEQ ID NO: 3 are composed of 7488 nucleotides with an open reading frame between the 1515$^{th}$ and 3527$^{th}$ nucleotides. Both SEQ ID NO: 2 and SEQ ID NO: 4 are composed of 671 amino acids.

EXPERIMENTAL DETAILS

Experiment 1: Preparation of MLV-RT-Q84A-D524N

1, Construction of Plasmid pTacRT-Q84A-D524N

The Q84A substitution was introduced into MLV-RT-D524N to generate MLV-RT-Q84A-D524N.

The Q84A mutation in the MLV-RT-D524N (Blain, S. W & Goff, S. P. (1995) *J. Virol.* 69, 4440-4452.) backbone was constructed by replacing the AflII-MfeI fragment of pTacRT-D524N (nt1467-2058) with two PCR-derived fragments AflII-EcoRIandEcoRI-MfeI. The 300 bp AflII-EcoRI fragment was generated using forward primer (5'GTGGAATTGTGAGCCGA)(SEQ ID NO: 5) and a mutation specific reverse primer Q84A-AP (5'CG GAATTCCCGCGTCCAACAGTCTCTGTA)(SEQ ID NO: 6) bearing silent mutations creating a restriction site; the 300 bp EcoRI-MfeI fragment was generated using reverse primer (5'TGGGAGTCTGGTCCAGG)(SEQ ID NO: 7) and a mutation specific forward primer Q84A-SP (5'CG GAATTCTGGTACCCTGCCAGTC)(SEQ ID NO: 8) bearing silent mutations creating the same restriction site as created in the 5' fragment. The codon for alanine was built in the mutation specific primers. The restriction sites built in the primers are underlined. The AflII-EcoRI fragment (nt1467-1770) and EcoRI-MfeI fragment (nt1770-2058) were inserted into a 6.9 kb vector, pTacRT-D524N, which was digested with AflII/-MfeI. The ligation mixture was transformed into *Escherichia coli* Top 10 and pTacRT-Q84A-D524N clones were picked based on restriction enzyme deigestion analysis. The result of nucleotide sequencing showed that the sequence of pTacRT-Q84A-D524N was the same as the sequence in SEQ ID NO: 1.

2, Expression of Recombinant Reverse Transcriptases in *Escherichia coli*

*Escherichia coli* BL21 cells transformed with pTacRT-Q84A-D524N were inoculated in LB medium containing 100 µg/ml ampicillin at 37° C. When the cells were grown to a density of OD$_{600}$ 0.5, IPTG was added to the medium at the final concentration of 0.5 mM to induce RT expression. The cells were cultured for additional 2-3 hours at 37° C. At the end of the induction, the cells were harvested by centrifugation and washed once with 50 mM ice-cold Tris-HCl (pH 7.5) for further RT purification.

3, Purification of the RT Proteins

Figure 1:
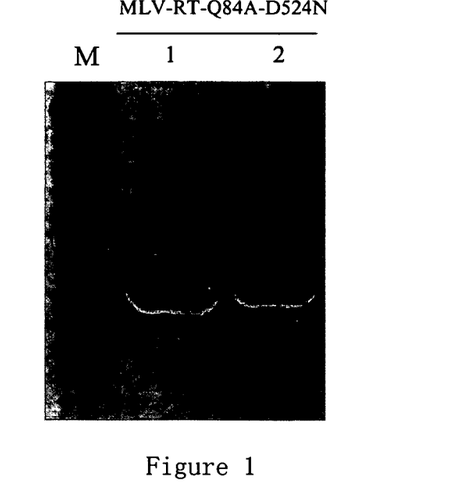
FIG. 1 SDS-PAGE analysis of purified MLV-RT-Q84A-D524N

The cells were resuspended in buffer A (20 mM sodium phosphate (pH 7.4), 0.5 M NaCl) containing lysozyme at a final concentration of 0.5 mg/ml and incubated on ice for 30 min. The suspension was briefly sonicated and then cleared of debris by centrifugation. After HiTrap chelating HP column (Pharmacia) purification, the purity of RT was higher than 80%, as analyzed by SDS-PAGE. The enzyme was purified to near homogeneity by MonoS (Pharmacia) fast protein liquid chromatography (FPLC), as analyzed by SDS-PAGE. MLV-RT-Q84A-D524N is a nearly homogenous band of 76 kD in the gel after Coomasia Brilliant Blue staining (FIG. 1). FIG. 1: M, Molecular Weight Standard; 1, 5/g protein; 2, 2/g protein.

4, Homopolymer Assays and Kinetic Analysis

Typical assays were performed at 37° C. using 10 ng of RT in 50 µl of reaction containing 60 mM Tris.HCl (pH 8.0), 75 mM NaCl, 0.7 mM MnCl$_2$, 5 mM DTT, 12 µg/ml poly(rA) template, 6 µg/ml oligo(dT)$_{18}$ primer, 10 µCi/ml $^{32}$P-labeled dTTP (1 Ci=37 GBq) and 12 µM unlabeled dTTP. At each time point, 4/1 of the reaction was removed and spotted on DE81 paper (Whatman). The paper was washed twice with 2× standard saline citrate (SSC), followed by scintillation counting.

Figure 2:
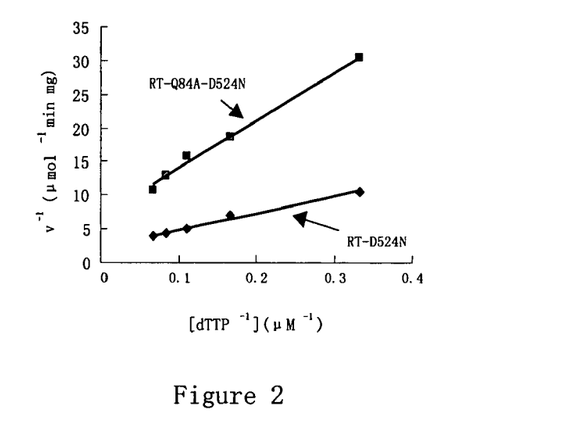
FIG. 2 Kinetic analysis of MLV-RT-Q84A-D524N and MLV-RT-D524N

To measure the kinetic parameters, the enzyme was added to the reaction mix to initiate the reaction. The radioactivity retained on the paper, in comparison with the total radioactivity in each sample, was used to determine the amount of dTTP incorporated into the product. The kinetic parameters were determined by double reciprocal plot (FIG. 2). While MLV-RT-Q84A-D524N and MLV-RT-D524N displayed comparable affinities (Km) for dTTP (11.04 µM and 12.94 µM, respectively), the catalytic activity (Vmax) for dTTP of MLV-RT-Q84A-D524N was 3.2 times the level of MLV-RT-D524N (0.41 µmol·min−1·ng−1 and 0.13 µmol·min−1·ng−1, respectively) (Table. 1).

TABLE 1

Comparason of Kinetic Patameters between MLV-RT-Q84A-D524N and MLV-RT-D524N

| Enzyme | Vmax (µmol · min$^{-1}$ · ng$^{-1}$) | Km (µM) |
|---|---|---|
| RT-D524N | 0.13 ± 0.04 | 12.94 ± 2.08 |
| RT-Q84A-D524N | 0.41 ± 0.04 | 11.05 ± 0.72 |

5, First Strand cDNA Synthesis:

Here we show the difference in first strand cDNA synthesis between MLV-RT-Q84A-D524N and MLV-RT-D524N.

Figure 3:
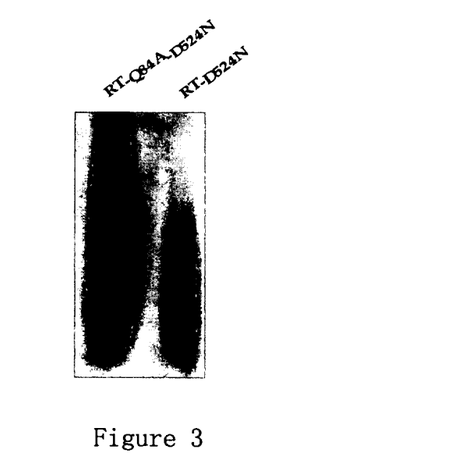
FIG. 3 The first strand cDNA synthesis by MLV-RT-Q84A-D524N and MLV-RT-D524N.

The total RNA of Rat-2 cells was isolated using the RNeasy kit (Qiagen) following the manufacturer's instructions. The first strand cDNA synthesis was performed in 20 µl of reaction containing 50 mM Tris.HCl (pH 8.0), 75 mM KCl, 3 mM MgCl$_2$, 5 mM DTT, 500 µM dNTPs, 20 u RNasin, 10 µCi α-$^{32}$P-dCTP (1 Ci=37 GBq), 1 µg of total RNA template. The reaction mixture was preheated at 42° C. for 2 min before 0.5 µg RT was added to initiate DNA synthesis. The reaction was carried out at 42° C. for 1 hour and then stopped by heating at 70° C. for 15 min. The products were analyzed by electrophoresis on a 1.4% alkaline agarose gel, followed by autoradiography. As shown in FIG. 3, RT-Q84A-D524N synthesizes longer and more cDNAs than RT-D524N.

Example 2

Preparation of MLV-RT-Q84N-D524N

1, Construction of Plasmid pTacRT-Q84N-D524N

The of Q84N substitution was introduced into MLV-RT-D524N to generate MLV-RT-Q84N-D524N.

The Q84N mutation in the MLV-RT-D524N (Blain, S. W & Goff, S. P. (1995) *J. Virol.* 69, 4440-4452) backbone was constructed by replacing the AflII-MfeI fragment of pTacRT-D524N (nt1467-2058) with two PCR-derived fragments AflEcoRI and EcoRI-MfeI. The 300 bp AflII-EcoRI fragment was generated using forward primer (5'GTGGAATTGTGAGCCGA)(SEQ ID NO: 5) and a mutation specific reverse primer Q84N-AP (5'CG GGATCCCGTTGTCCAACAGTCTCTGTA)(SEQ ID NO:6) bearing silent mutations creating a restriction site; the 300 bp EcoRI-MfeI fragment was generated using reverse primer (5'TGGGAGTCTGGTCCAGG)(SEQ ID NO: 7) and a mutation specific forward primer Q84N-SP (5'CG GGATCCTGGTACCCTGCCAGTC)(SEQ ID NO: 8) bearing silent mutations creating the same restriction site as created in the 5' fragment. The codon for asparagine was built in the mutation specific primers. The restriction sites built in the primers are underlined. The AflII-BamHI fragment (nt1467-1770) and BamHI-MfeI fragment (nt1770-2058) were inserted into a 6.9 kb vector, pTacRT-D524N, which was digested with AflII and MfeI. The result of nucleotide sequencing showed that the sequence of pTacRT-Q84N-D524N was the same as the sequence in SEQ ID NO: 3.

2, Expression of Recombinant Reverse Transcriptases in *E. coli*

*Escherichia coli* BL21 cells transformed with pTacRT-Q84N-D524N were inoculated in LB medium containing 100 µg/ml ampicillin at 37° C. When the cells were grown to a density of $OD_{600}$ 0.5, IPTG was added to the medium at the final concentration of 0.5 mM to induce RT expression. The cells were cultured for additional 2-3 hours at 37° C. At the end of the induction, the cells were harvested by centrifugation and washed once with 50 mM ice-cold Tris-HCl (pH 7.5) for further RT purification.

3, Purification of Recombinant Reverse Transcriptase

Figure 4:
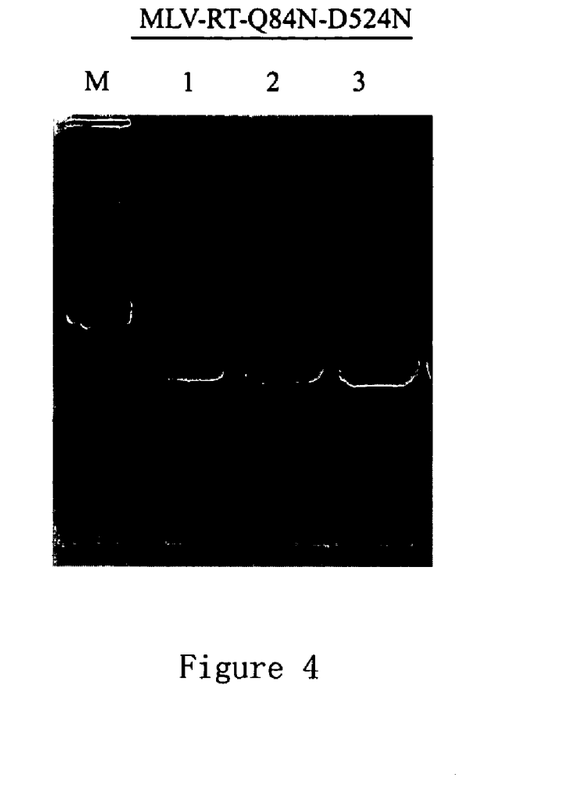
FIG. 4 SDS-PAGE analysis of purified MLV-RT-Q84N-D524N

The cells were resuspended in buffer A (20 mM sodium phosphate (pH 7.4), 0.5 M NaCl) containing lysozyme at a final concentration of 0.5 mg/ml and incubated on ice for 30 min. The suspension was briefly sonicated and then cleared of debris by centrifugation. After HiTrap chelating HP column (Pharmacia) purification, the purity of RT was higher than 80%, as analyzed by SDS-PAGE. The enzyme was purified to near homogeneity by MonoS (Pharmacia) fast protein liquid chromatography (FPLC), as analyzed by SDS-PAC-E. MLV-RT-Q84N-D524N is a nearly homogenous band of 76 kD in the gel after Coomasia Brilliant Blue staining (FIG. 4). FIG. 4: M, Molecular Weight Standard; 1, 1 µg protein; 2, 2 µg protein; 3, 5 µg protein.

5, Homopolymer Substrate Assays

Typical assays were performed at 37° C. using 10 ng of RT in 50 µl of reaction containing 60 mM Tris.HCl (pH 8.0), 75 mM NaCl, 0.7 mM $MnCl_2$, 5 mM DTT, 12 µg/ml poly(rA) template, 6 µg/ml oligo(dT)$_{18}$ primer, 10 µCi/ml $^{32}$P-labeled dTTP (1 Ci=37 GBq) and 12 µM unlabeled dTTP. At each time point, 4 µl of the reaction was removed and spotted on DE81 paper (Whatman). The paper was washed twice with 2× standard saline citrate (SSC), followed by autoradiography.

Figure 5:
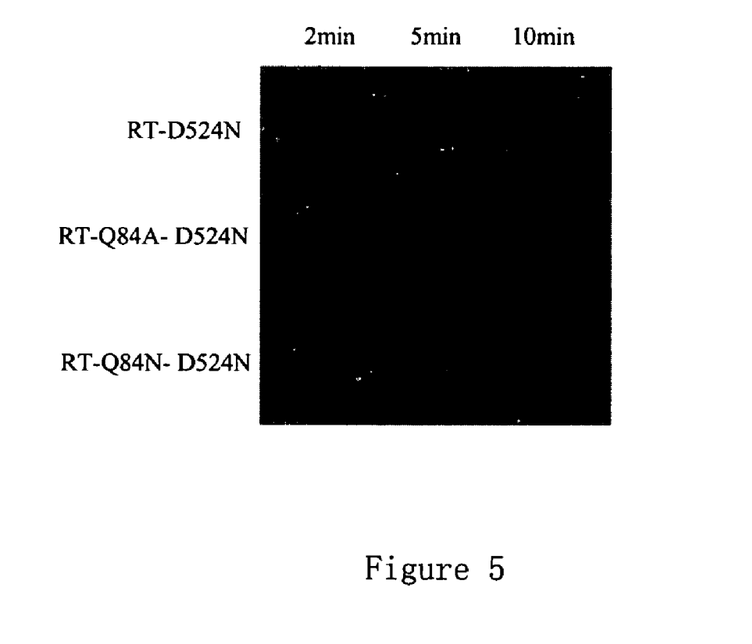
FIG. 5 DNA polymerase activity assay of MLV-RT-Q84N-D524N

MLV-RT-Q84N-D524N manifested higher activities than RT-WT-H but had a similar activity to MLV-RT-Q84A-D524N (FIG. 5).

Application

Based on the high-resolution structure of a catalytically active fragment of MLV-RT, we discovered that the 84th amino acid residue of this enzyme, glutamine (Q84), which is located in the active site, regulates the catalytic activity of the enzyme. The long side chain of this residue presumably blocks the elongation of the products and affects the DNA polymerase activity and processivity. By replacing Q84 with an amino acid residue with a side chain shorter than that of glutamine, we generated a new enzyme, MLV-RT-Q84X, wherein X is an amino acid with a side chain shorter than that of glutamine, like alanine (Ala), serine (Ser), asparagine (Asn), or aspartic acid (Asp) and so on. In this invention the Q84X substitution was also introduced into MLV-RT-D524N, to generate MLV-RT-Q84X-D524N. These recombinant murine leukemia virus reverse transcriptases demonstrate higher enzyme activity and processivity than MLV-RT-D524N (Superscript II). These new enzymes are expected to be widely used in the field of biotechnology, particularly for cDNA synthesis.

The invention claimed is:

1. A variant of the Moloney murine leukemia virus reverse transcriptase of SEQ ID NO:2, wherein said variant has the amino acid sequence of SEQ ID NO:2 except having the amino acid X at position 84, which is an amino acid with a side chain shorter than that of glutamine, and said variant has reverse transcriptase activity.

2. The variant of claim 1, except having the amino acid asparagine at position 524 replaced with the amino acid aspartic acid.

3. The variant of claim 1, wherein the amino acid X is alanine, serine, aspartic acid or asparagine.

4. The variant of claim 3, wherein the amino acid X is alanine.

5. The variant of claim 2, wherein the amino acid X is alanine, serine, aspartic acid, or asparagine.

6. The variant of claim 5, wherein the amino acid is alanine.

7. A variant of the wild type Moloney murine leukemia virus reverse transcriptase having the amino acid sequence of SEQ ID NO:9, wherein said variant has the amino acid sequence of SEQ ID NO:9 except having the amino acid mutation at position 84, such that the glutamine is replaced with amino acid X, wherein said amino acid X is an amino acid with side chain shorter than that of glutamine, and said variant has reverse transcriptase activity.

* * * * *